US011471694B2

(12) United States Patent
Hwang

(10) Patent No.: US 11,471,694 B2
(45) Date of Patent: Oct. 18, 2022

(54) PLASMA ELECTRODE PAD FOR TREATMENT OF WOUNDS AND PLASMA TREATMENT DEVICE

(71) Applicant: SJ GLOBAL CO., LTD., Bucheon-si (KR)

(72) Inventor: Yu An Hwang, Bucheon-si (KR)

(73) Assignee: SJ GLOBAL CO., LTD., Bucheon-si (KR)

(*) Notice: Subject to any disclaimer, the term of this patent is extended or adjusted under 35 U.S.C. 154(b) by 870 days.

(21) Appl. No.: 16/338,497

(22) PCT Filed: Feb. 8, 2019

(86) PCT No.: PCT/KR2019/001569
§ 371 (c)(1),
(2) Date: Apr. 1, 2019

(87) PCT Pub. No.: WO2020/158983
PCT Pub. Date: Aug. 6, 2020

(65) Prior Publication Data
US 2021/0361963 A1 Nov. 25, 2021

(30) Foreign Application Priority Data
Jan. 29, 2019 (KR) .................. 10-2019-0011127

(51) Int. Cl.
A61N 1/44 (2006.01)
A61N 1/04 (2006.01)
H05H 1/24 (2006.01)

(52) U.S. Cl.
CPC ............. *A61N 1/44* (2013.01); *A61N 1/0492* (2013.01); *H05H 1/2406* (2013.01); *A61N 1/0468* (2013.01); *H05H 2245/34* (2021.05)

(58) Field of Classification Search
None
See application file for complete search history.

(56) References Cited

U.S. PATENT DOCUMENTS

| | | | | |
|---|---|---|---|---|
| 6,339,290 B1* | 1/2002 | Nakaya | ............... | H01L 51/5221 313/506 |
| 7,767,167 B2* | 8/2010 | Keras | ..................... | B01D 53/32 422/186.04 |
| 8,029,105 B2* | 10/2011 | Sieber | .................... | B41J 2/1631 347/56 |
| 8,343,090 B2* | 1/2013 | Rooks | .................. | A61B 18/042 606/49 |
| 8,708,651 B2* | 4/2014 | Greenblatt | ........... | H05H 1/2406 416/185 |

(Continued)

FOREIGN PATENT DOCUMENTS

KR    10-1292268 B1    8/2013

*Primary Examiner* — Srinivas Sathiraju
(74) *Attorney, Agent, or Firm* — Revolution IP, PLLC

(57) ABSTRACT

A floating type plasma electrode pad includes the plasma electrode made of a conductive metal thin film, a flexible dielectric thin film layered on the plasma electrode, and made of a polymer material, the dielectric thin film being spaced apart from the skin by a predetermined distance such that microdischarge is generated in a space defined between the dielectric thin film and the skin, and a spacer layered on the dielectric thin film, to space the dielectric film from the skin by the predetermined distance.

9 Claims, 17 Drawing Sheets

(56) References Cited

U.S. PATENT DOCUMENTS

| | | | |
|---|---|---|---|
| 9,117,636 B2* | 8/2015 | Koo | H01J 37/32541 |
| 9,498,637 B2* | 11/2016 | Sanders | A61B 18/042 |
| 9,693,441 B2* | 6/2017 | Patelli | H05H 1/2406 |
| 9,784,712 B2* | 10/2017 | Persson | H05H 1/2406 |
| 11,195,748 B2* | 12/2021 | Uzoh | H01L 23/5226 |
| 2008/0110744 A1* | 5/2008 | Girard | C01B 7/20 |
| | | | 204/194 |
| 2009/0102886 A1* | 4/2009 | Sieber | B41J 2/1637 |
| | | | 347/45 |
| 2010/0329838 A1* | 12/2010 | Greenblatt | F01D 5/145 |
| | | | 415/1 |
| 2012/0259270 A1* | 10/2012 | Wandke | H05H 1/24 |
| | | | 604/23 |
| 2013/0038196 A1* | 2/2013 | Tixhon | H01J 37/3255 |
| | | | 313/352 |
| 2013/0084409 A1* | 4/2013 | Vangeneugden | D06M 10/025 |
| | | | 118/718 |
| 2015/0157870 A1* | 6/2015 | Kalghatgi | A61F 7/02 |
| | | | 604/23 |
| 2016/0295676 A1* | 10/2016 | Patelli | H05H 1/2406 |
| 2016/0302906 A1* | 10/2016 | Lam | H01J 37/32366 |
| 2016/0331989 A1* | 11/2016 | Cho | A61N 1/326 |
| 2018/0099149 A1* | 4/2018 | Pai | A61L 2/14 |
| 2020/0246496 A1* | 8/2020 | Mazzeo | A61L 2/0094 |
| 2020/0396820 A1* | 12/2020 | de Vries | A61N 1/0476 |
| 2020/0406016 A1* | 12/2020 | Kalghatgi | A61M 37/0015 |
| 2021/0022234 A1* | 1/2021 | Polak | A61B 18/042 |
| 2021/0361963 A1* | 11/2021 | Hwang | A61N 1/0492 |

* cited by examiner

[FIG.1a]
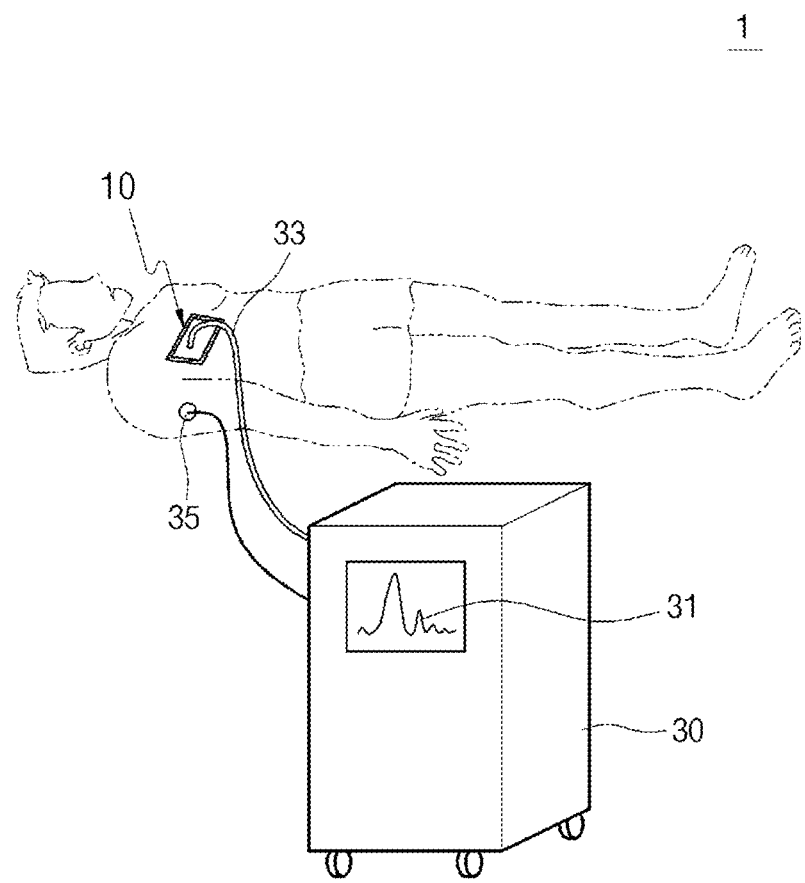

[FIG.1b]
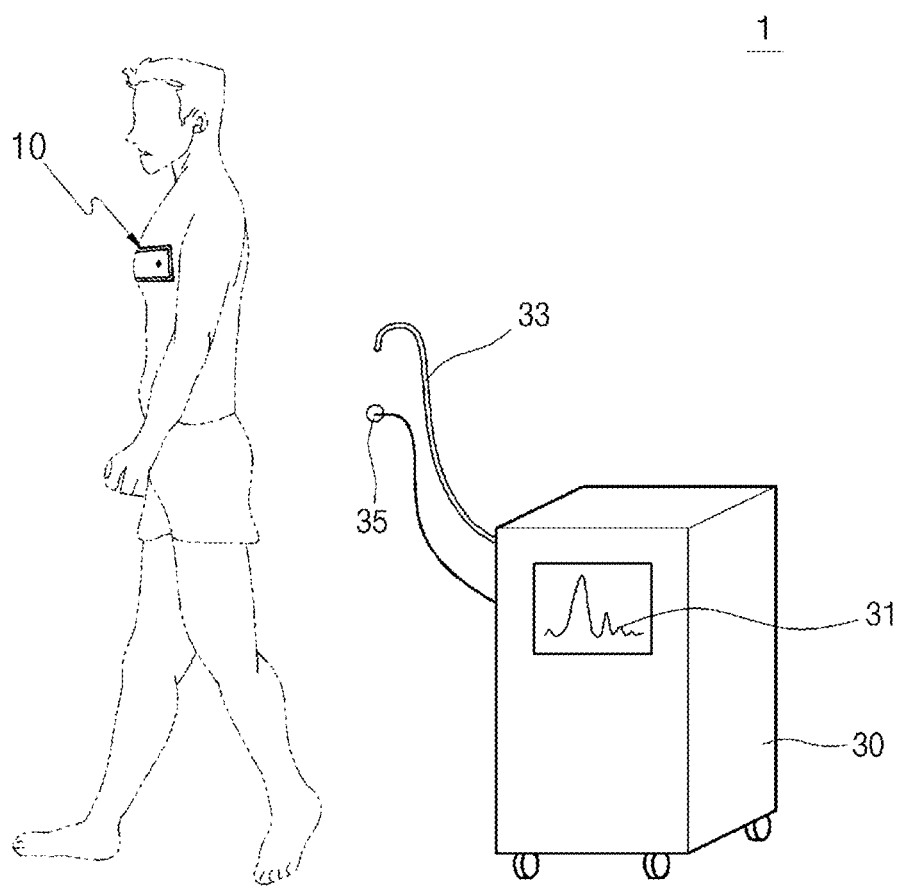

[FIG.2]
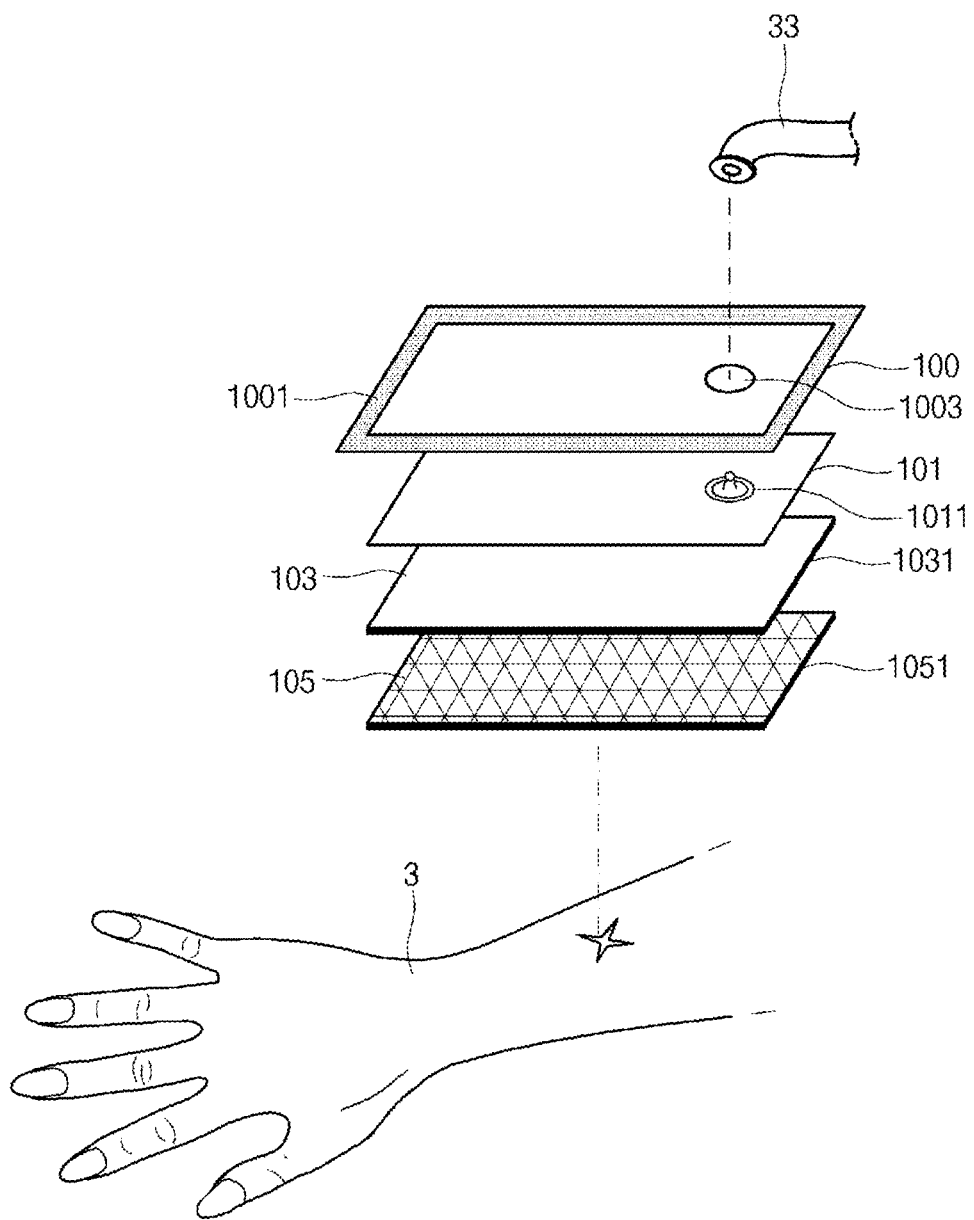

[FIG.3]
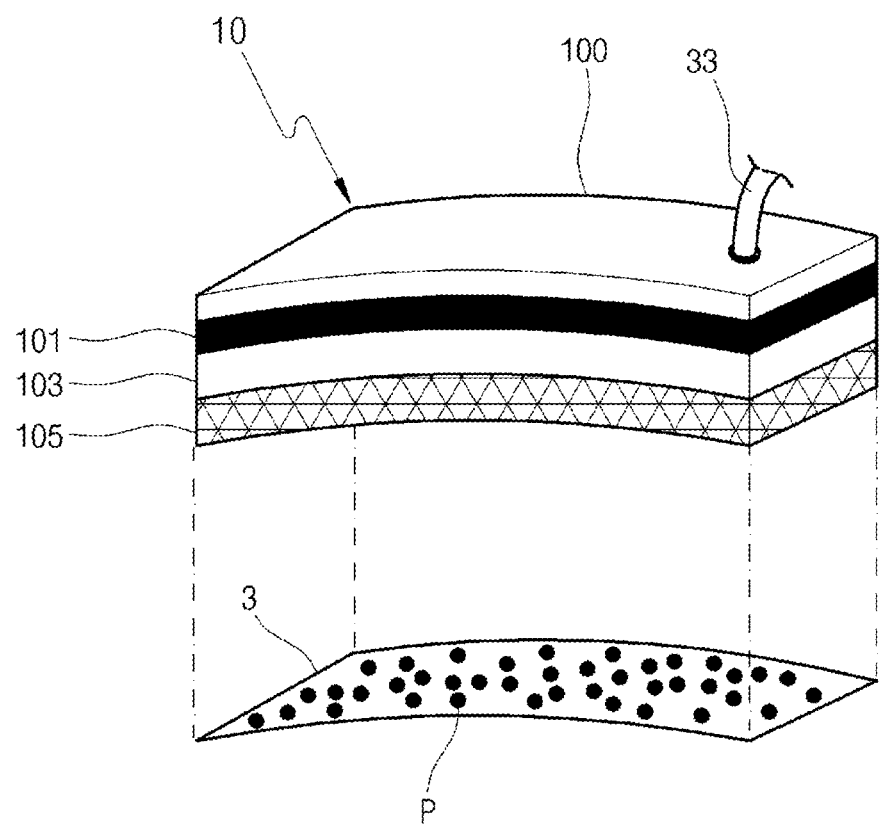

[FIG.4a]
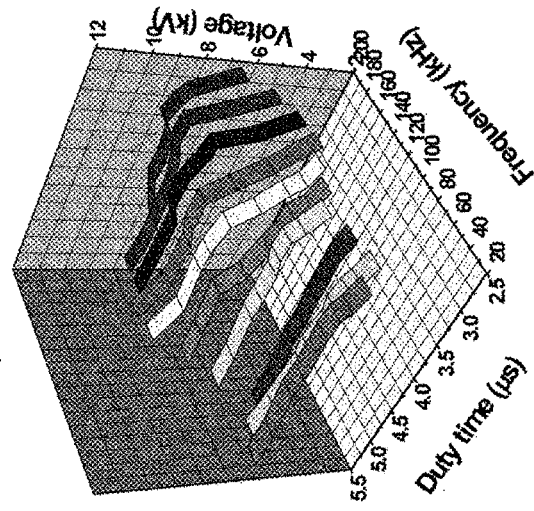
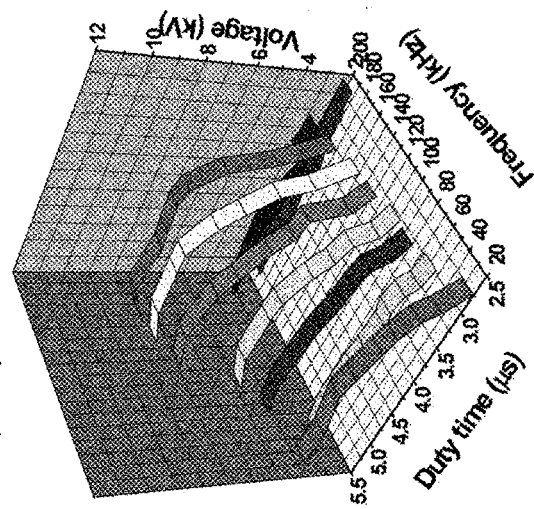

[FIG.4b]
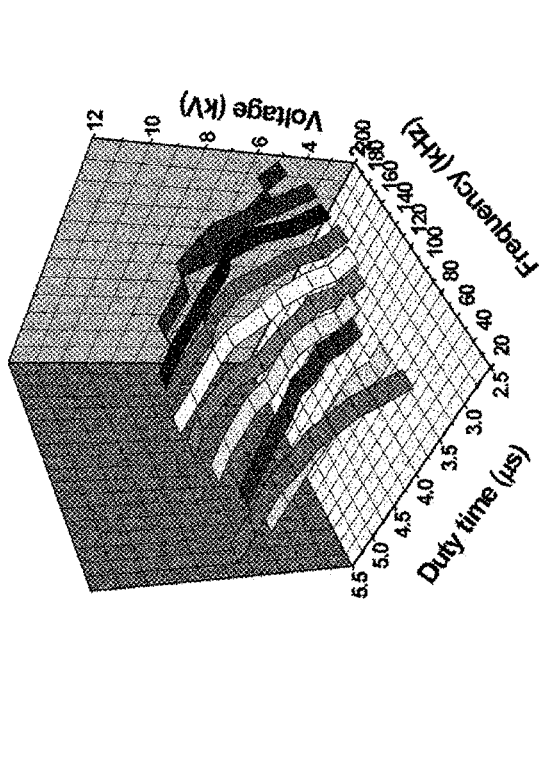
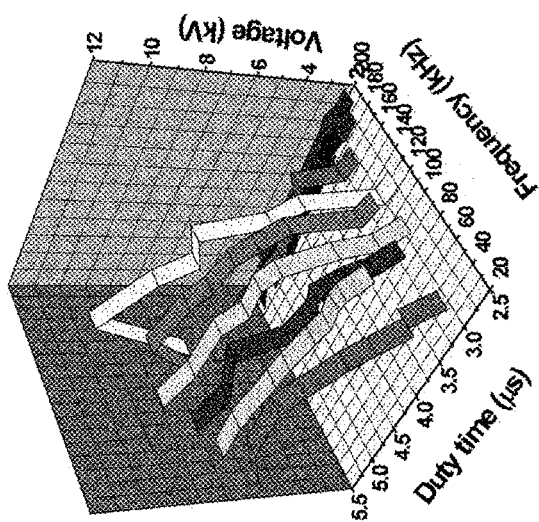

[FIG.5]
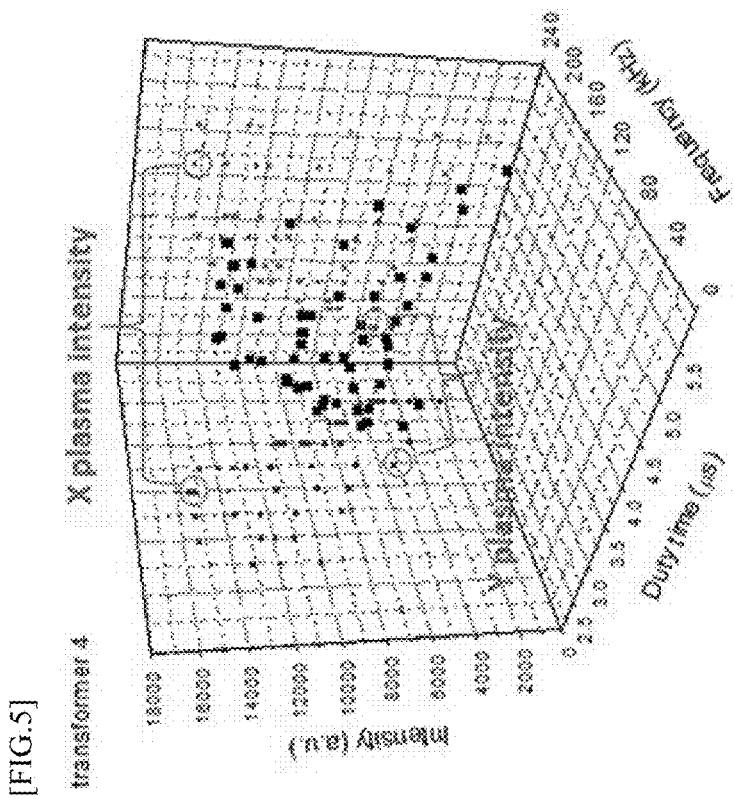
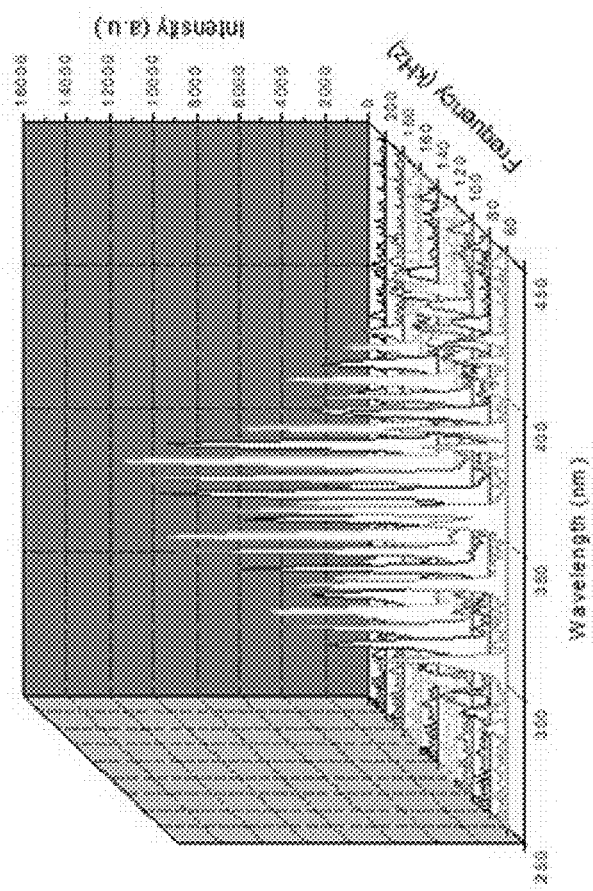

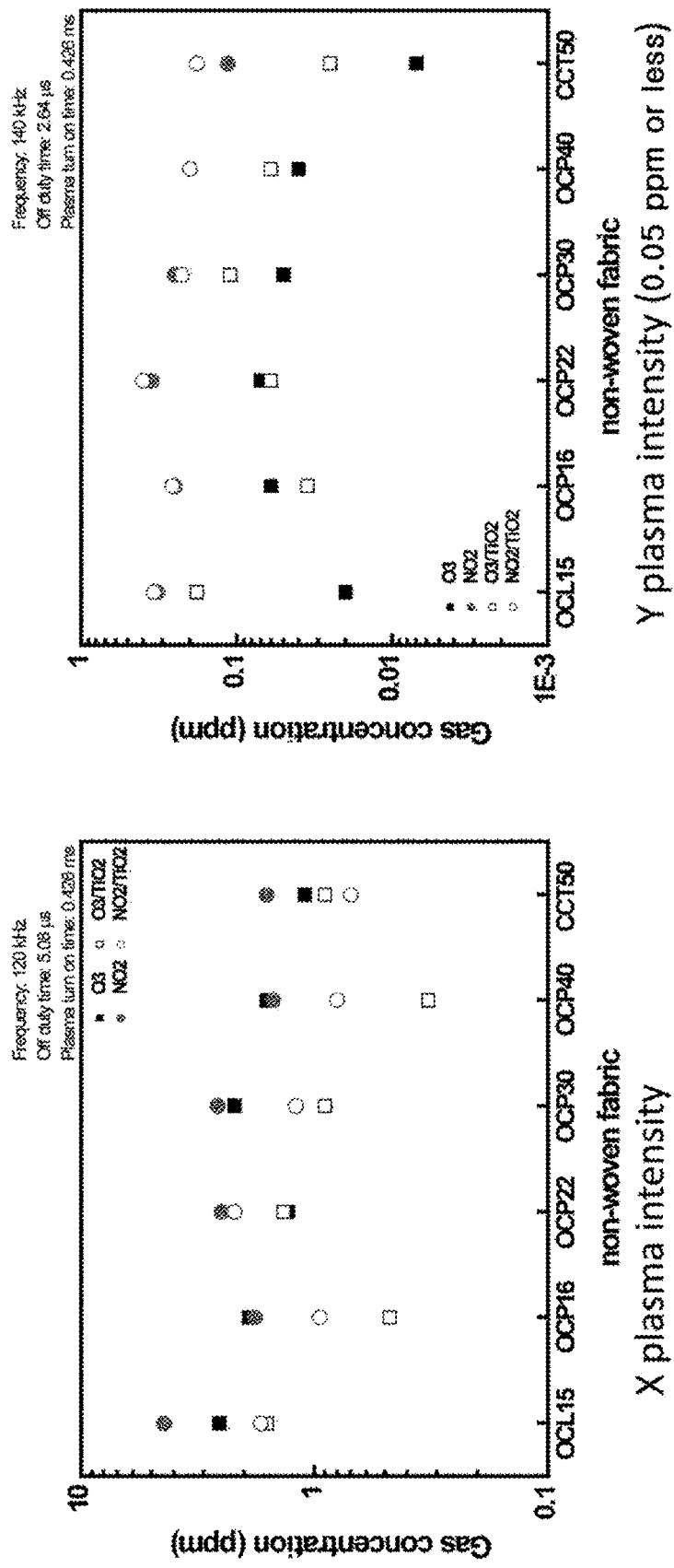
[FIG.6]

[FIG.7]
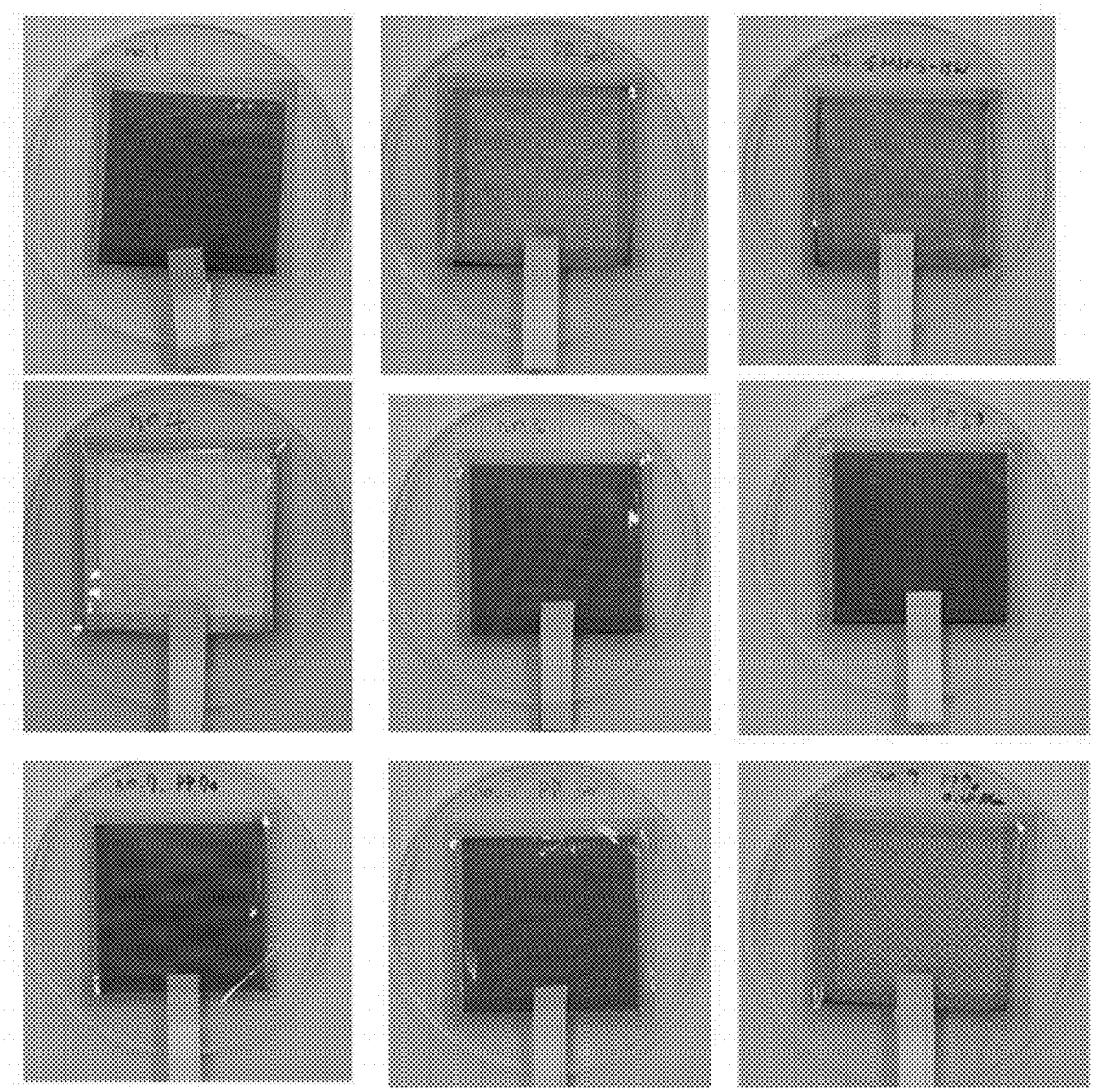

[FIG.8]
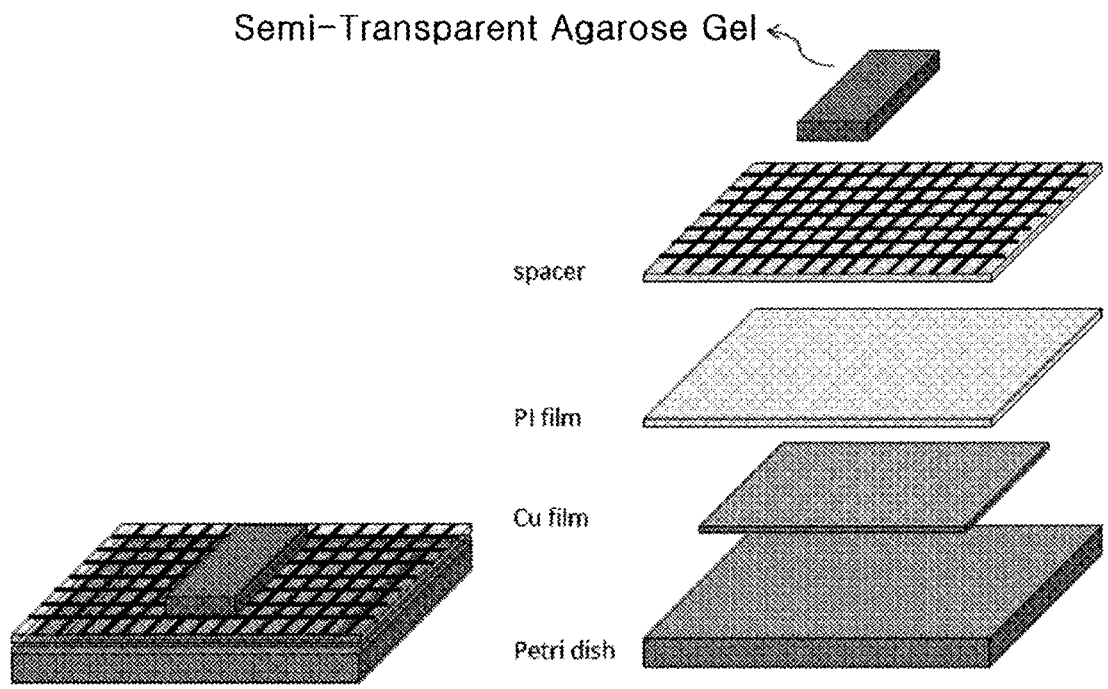

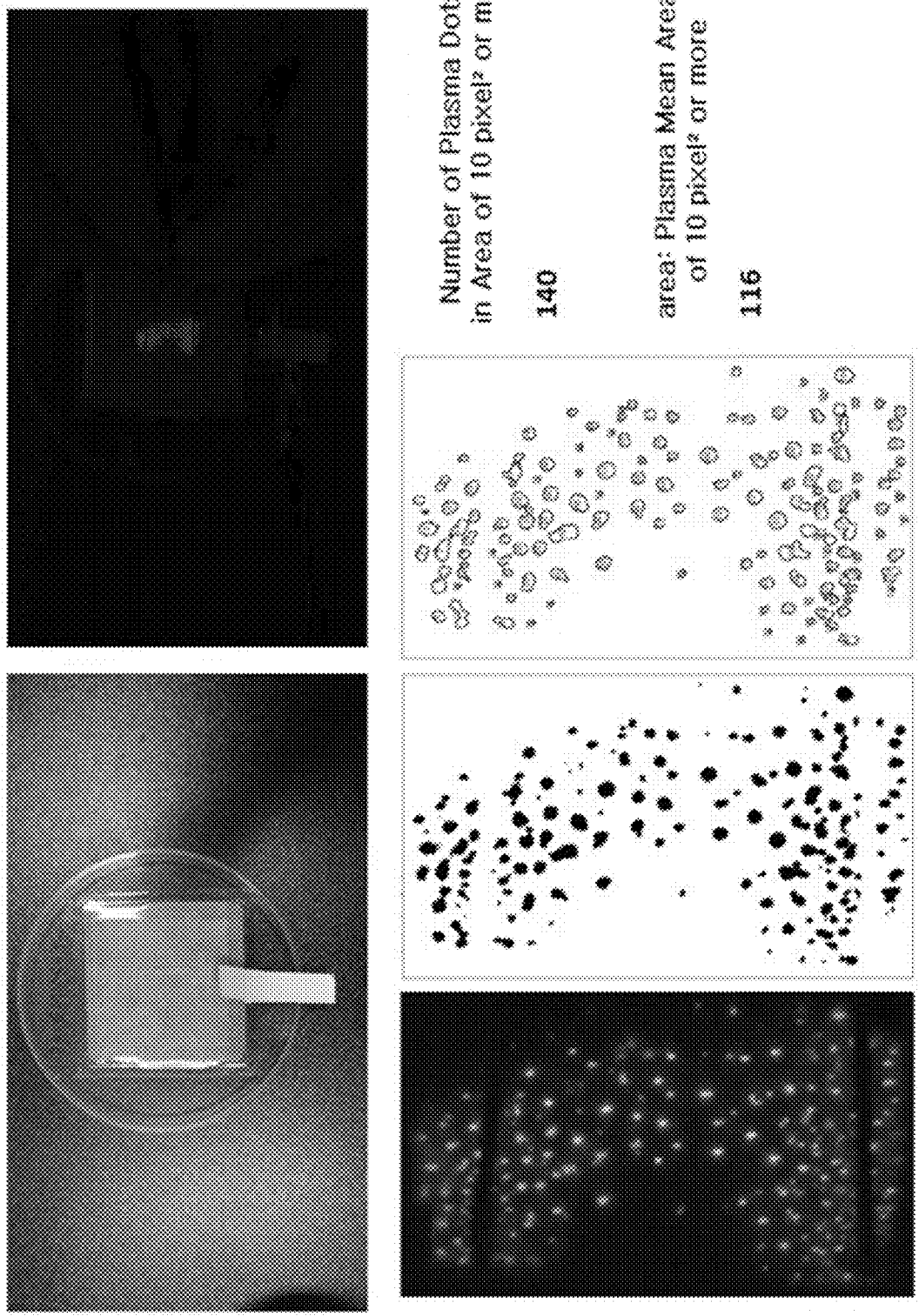
[FIG.9]

[FIG.10]
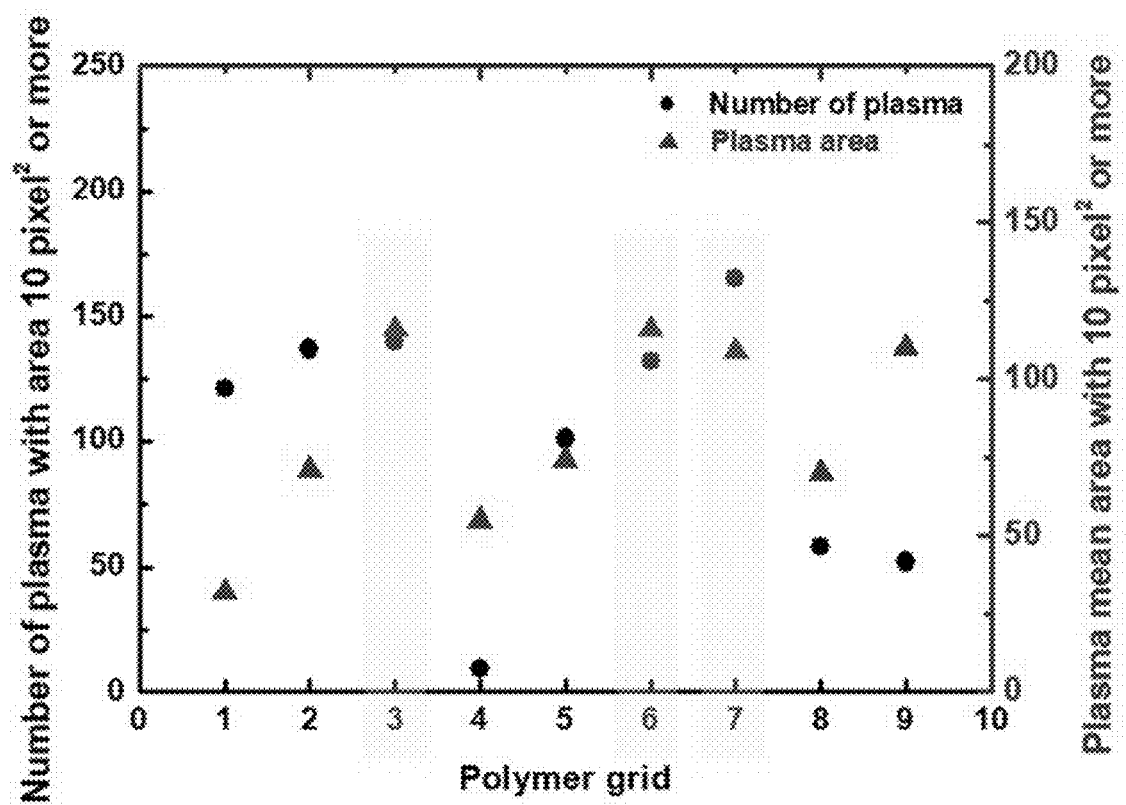

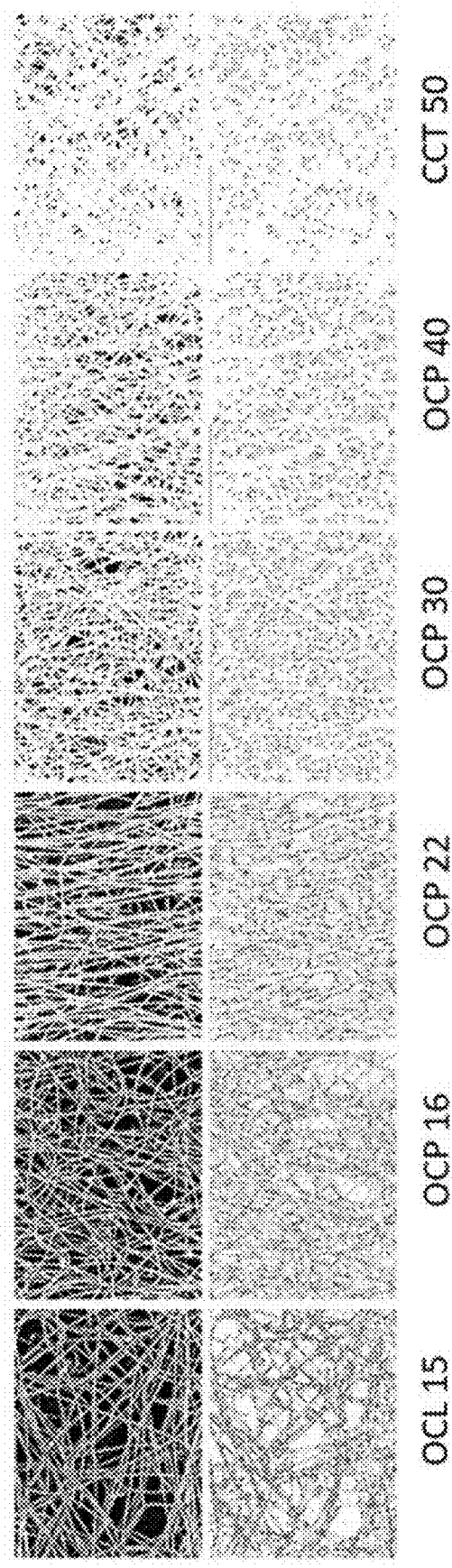
[FIG.11]

[FIG.12]
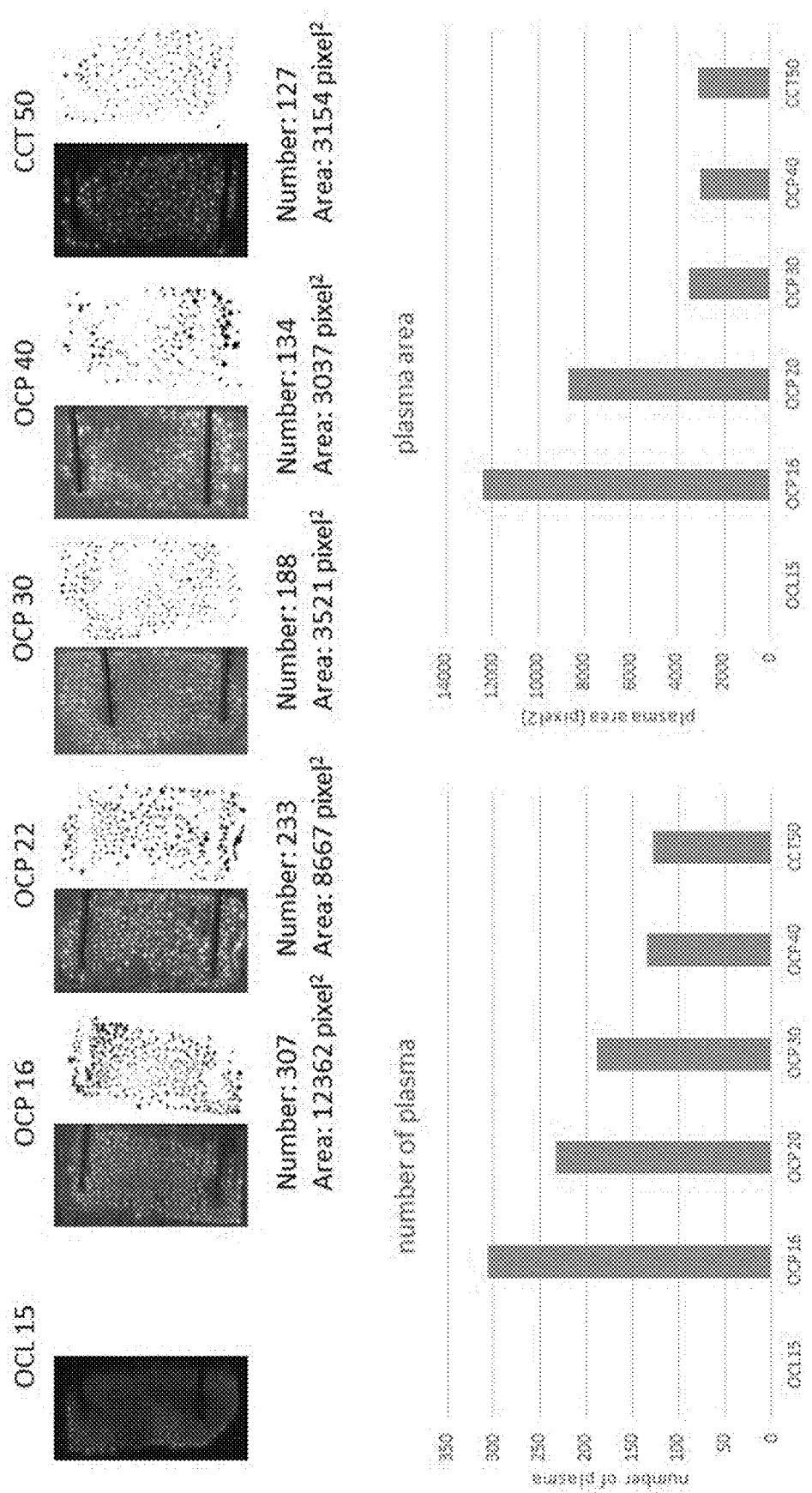

[FIG.13]
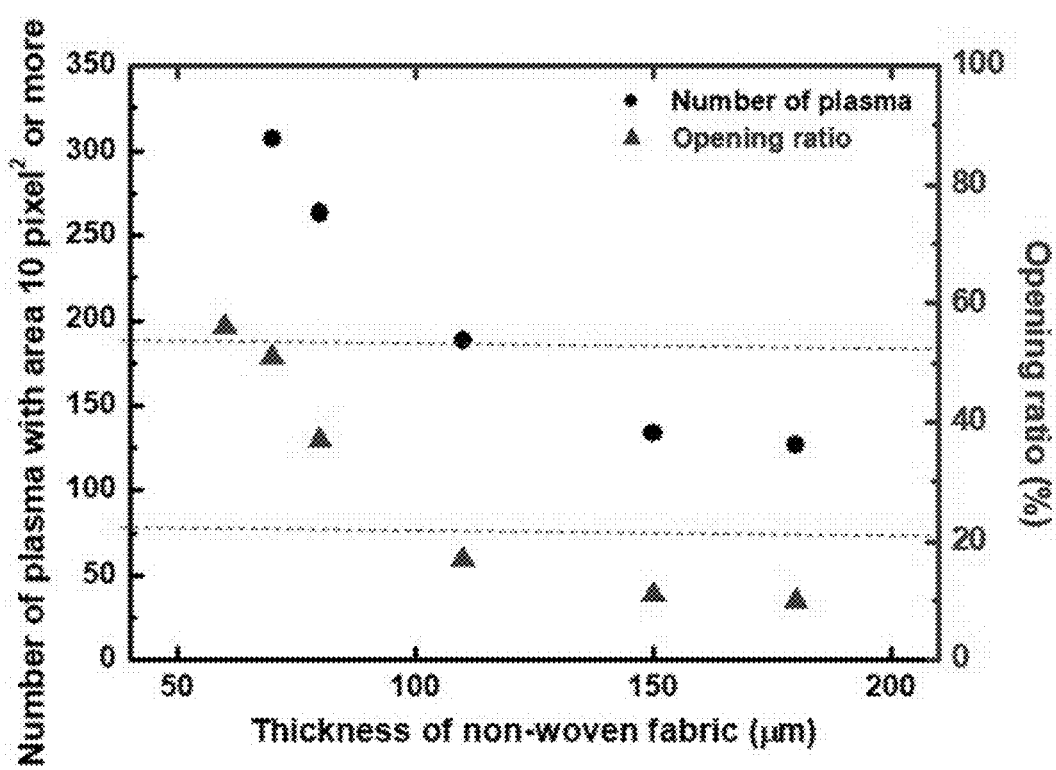

[FIG.15]
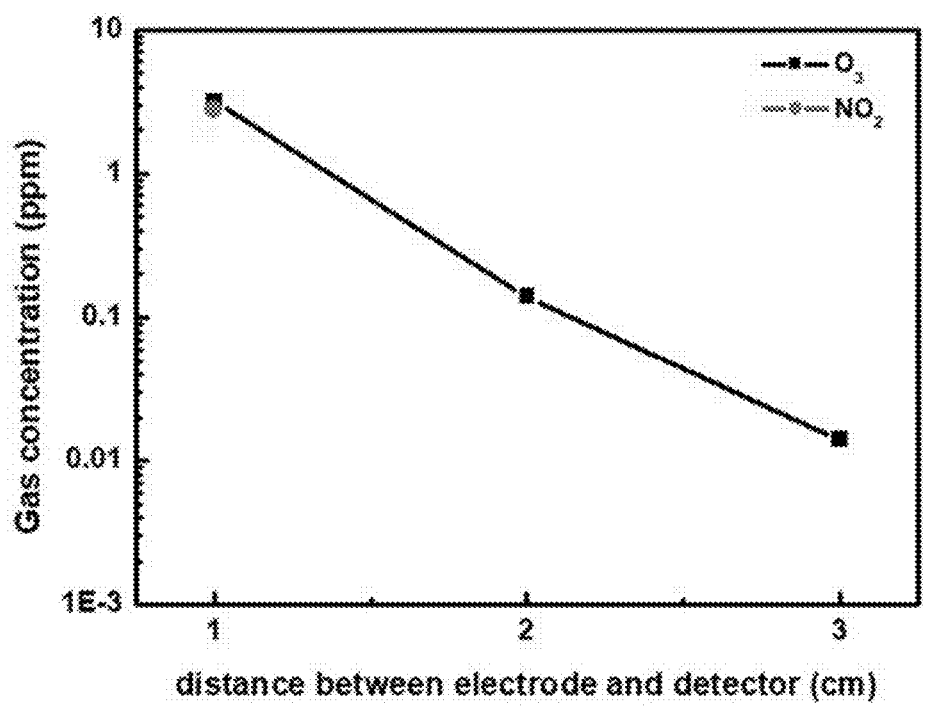

PLASMA ELECTRODE PAD FOR TREATMENT OF WOUNDS AND PLASMA TREATMENT DEVICE

TECHNICAL FIELD

The present invention relates to a plasma treatment device usable for medical treatment, and more particularly to a plasma electrode pad attachable to the skin, like a pad, to assist in sterilization of a wound and regeneration of tissue.

BACKGROUND ART

Recently, atmospheric plasma has been applied not only to research in engineering and biology, but also to conversing technologies associated with medical appliances. When a high voltage is applied between two electrodes in an electrode module for generating plasma, electric discharge occurs in a space between the electrodes and, as such, ionization of reactive gas occurs, thereby generating plasma. The plasma generated as mentioned above contains various functional ions. It has been reported that reactive species produced in plasma have significant effects in association with application thereof to various treatments such as sterilization, wound healing, stopping of bleeding, apoptosis and the like. Reactive oxygen species are effective in sterilization, whereas reactive nitrogen species are effective in maintenance of cellular homeostasis. Conventionally, plasma technologies have been applied to medical appliances in some fields for tooth whitening, etc. However, there are few or no commercially available medical plasma appliances in which plasma acts directly on the human body, to perform treatment functions for sterilization, cleaning, cell regeneration, or the like.

In the case of a plasma electrode module for use in medical appliances, the following technical subjects to be solved should be taken into consideration. Generally, 90% or more of plasma research is associated with direct barrier discharge (DBD) type plasma and corona jet type plasma. In the conventional plasma modules, consumption of gas supplied for plasma discharge, such as helium or argon, is great and, as such, additional equipment for supply of gas is required. To this end, a simplified system for integrating plasma into various technical fields should be developed.

Meanwhile, most research into atmospheric plasma generated using air in place of gas for discharge is research into DBD structures and torch type electrode structures. In conventional electrode structures, there is a problem in that, since the spacing between the electrodes is small or the plasma treatment cross-sections of the electrodes are small, the electrodes should be designed to have a great size in order to achieve large-area discharge while enhancing electric power efficiency.

As related art literature, Korean Registered Patent No. 10-1292268 (hereinafter, simply referred to as "related patent") discloses a parallel-driven microplasma wound treatment device. The related patent illustrates a plasma module configured taking into consideration various areas and portability, in order to solve issues arising in association with application of plasma for medical treatment. Plasma electrode modules developed up to the present for direct application thereof to a human body generally employ a direct DBD model, as in the related patent. The direct DBD model has a structure wherein both an electrode, to which electric power is applied, and a ground electrode are configured in the plasma electrode module. Referring to the related patent, the above-mentioned electrodes correspond to a first electrode 1a and a second electrode 1b. Plasma is generated in a space between the two electrodes.

The direct DBD model is configured to radiate plasma generated between the electrodes onto the skin. In this regard, the direct DBD model may be suitable for a handled type. However, the direct DBD model has drawbacks in terms of electrode structure when the direct DBD model is used to embody a pad type electrode module. The direct DBD model does not use a system in which the skin is directly irradiated with plasma, but uses a system in which the skin is indirectly irradiated with plasma between electrodes. For this reason, the direct DBD model may require more or less high electric power for generation of plasma effective for treatment. In this case, medical equipment having treatment purposes may have a problem in that the medical equipment may not meet various requirements for approval associated with safety.

Plasma devices inevitably emit ozone in an ionization process for generation of plasma. Ozone is a toxic material fatal to humans when the human body intakes the material through respiration. When plasma of higher intensity is generated, an increased amount of ozone is emitted. To this end, it is desired that plasma electrode modules for medical treatment be embodied to achieve a desired treatment efficiency in spite of generation of plasma in a minimum amount, in accordance with direct formation of plasma on the skin. During this process, emission of ozone caused by generation of plasma should also be minimized. In accordance with current trends of approval in home and abroad, there are no guidelines in association with an evaluation method for physical therapy devices for wound treatment using plasma in any country in the world. Although scientific research has been conducted for a long time in association with plasma, any product embodying application of plasma to a medical device for physical therapy has not been available yet.

Plasma involves both production of active oxygen species suitable for treatment and emission of ozone that may be fatal to humans. In designing a commercially available medical appliance using plasma, the electrode structure and function of the medical appliance should be importantly discussed. Briefly, in a plasma device capable of performing a medical treatment function, structures of electrodes, plasma generation efficiency and suppression of ozone emission may function as great problems associated with commercial availability of the plasma device.

To this end, the applicant invented a plasma pad having a floating electrode structure in which the skin of a human body functions as a ground electrode such that plasma is directly generated between the skin and an electrode, thereby being capable of exhibiting superior electromagnetic stability even when the plasma pad is applied to the skin in an attached manner, and suppressing emission of ozone.

DISCLOSURE

Technical Problem

Therefore, the present invention has been made in view of the above problems, and it is an object of the present invention to provide a plasma electrode pad capable of performing medical treatment using plasma formed on the skin, in a state of being attached to the skin, and a plasma treatment device using the plasma electrode pad.

Technical Solution

In accordance with an aspect of the present invention, the above and other objects can be accomplished by the provision of a floating type plasma electrode pad using the skin of a human body as a ground electrode such that plasma is generated between the skin of the human body and a plasma electrode disposed near the skin of the human body in accordance with a voltage applied to the plasma electrode, including the plasma electrode made of a conductive metal thin film, a flexible dielectric thin film layered on the plasma electrode, and made of a polymer material, the dielectric thin film being spaced apart from the skin of the human body by a predetermined distance such that microdischarge is generated in a space defined between the dielectric thin film and the skin of the human body, and a spacer layered on the dielectric thin film, to space the dielectric film from the skin of the human body by the predetermined distance, wherein the spacer is made of a fiber material to form multiple layers of fiber bundles.

In accordance with another aspect of the present invention, there is provided a floating type plasma treatment device using the skin of a human body as a ground electrode such that plasma is generated between the skin of the human body and a plasma electrode disposed near the skin of the human body in accordance with a voltage applied to the plasma electrode, including a floating type plasma electrode pad including the plasma electrode made of a conductive metal thin film, a flexible dielectric thin film layered on the plasma electrode, and made of a polymer material, the dielectric thin film being spaced apart from the skin of the human body by a predetermined distance such that microdischarge is generated in a space defined between the dielectric thin film and the skin of the human body, and a spacer layered on the dielectric thin film, to space the dielectric film from the skin of the human body by the predetermined distance, a power supply for supply electric power to the plasma electrode at a predetermined duty ratio, and a ground pad connected to the power supply, and adapted to contact the skin of the human body, whereby plasma having an electromagnetic wave emission amount suitable for the human body under a DC power condition.

In accordance with another aspect of the present invention, there is provided a floating type plasma electrode pad using the skin of a human body as a ground electrode such that plasma is generated between the skin of the human body and a plasma electrode disposed near the skin of the human body in accordance with a voltage applied to the plasma electrode, including the plasma electrode made of a conductive metal thin film, a flexible dielectric thin film layered on the plasma electrode, and made of a polymer material, the dielectric thin film being spaced apart from the skin of the human body by a predetermined distance such that microdischarge is generated in a space defined between the dielectric thin film and the skin of the human body, and a spacer layered on one surface of the dielectric thin film, to space the dielectric film from the skin of the human body by the predetermined distance, the spacer having a predetermined opening ratio, wherein the spacer contacts the skin at the other surface thereof such that plasma is directly irradiated on the skin through cavities formed at the spacer in a predetermined opening ratio, and the irradiation of the plasma has a dot-shaped form by virtue of the cavities.

Advantageous Effects

In accordance with the present invention, plasma is generated through cavities of the spacer contacting the skin and, as such, there may be an advantage in that plasma for treatment is directly generated in a wound area.

In addition, in accordance with the present invention, plasma for treatment is generated using customized DC power and, as such, superior electromagnetic stability is obtained, as compared to the case of using AC power. Furthermore, there may be an advantage in that plasma treatment may be carried out using low electric power.

Furthermore, in accordance with the present invention, a hygienic fiber material exhibiting a contact ability to a wound area is used as the spacer. In this case, fiber bundles of multiple layers form cavities particularly suitable for generation of plasma. In addition, the spacer exhibits an ozone absorption property because the spacer is made of a fiber material. There may also be an advantage in that the efficiency of coating a photocatalyst or an active catalyst over fiber bundles of multiple layers may be maximized.

In addition, the plasma electrode pad to be attached to a wound area has a simple configuration because the plasma electrode pad is of a floating type and, as such, a separate ground electrode is unnecessary. In accordance with the present invention, the plasma electrode pad may be disposable. In accordance with the present invention, plasma treatment is carried out under the condition that the plasma electrode pad is coupled to the power supply. After treatment, the plasma electrode pad may be separated from the power supply. In connection with this, the plasma electrode pad may be maintained in a state of being attached to the wound area, after completion of the plasma treatment conducted in a power connection state. In this case, since the contact surface of the plasma electrode pad is formed by the fiber material of the non-woven fabric, and the plasma electrode pad is light by virtue of a simple electrode structure thereof, there may be an advantage in that the patient may enjoy daily life under the condition that regeneration of tissue and hygiene for wound healing are ensured.

DESCRIPTION OF DRAWINGS

The above and other objects, features and other advantages of the present invention will be more clearly understood from the following detailed description taken in conjunction with the accompanying drawings, in which:

FIG. 1A illustrates a plasma treatment device according to an embodiment of the present invention, to show a plasma treatment state of the plasma treatment device;

FIG. 1B illustrates the plasma treatment device according to the embodiment of the present invention, to show a state of a plasma electrode pad used after plasma treatment;

FIG. 2 is an exploded perspective view of the plasma electrode pad according to the illustrated embodiment of the present invention;

FIG. 3 illustrates operation of a plasma electrode pad according to the illustrated embodiment of the present invention;

FIG. 4A shows identified results obtained after an experiment is conducted for four transformers having different turn ratios while varying frequency (kHz) and duty ratio (µs), to identify conditions that high output characteristics are maintained, and particularly shows identified results of power characteristics of transformers #1 and #2;

FIG. 4B shows identified results obtained after an experiment is conducted for four transformers having different turn ratios while varying frequency (kHz) and duty ratio (µs), to identify conditions that high output characteristics are maintained, and particularly shows identified results of power characteristics of transformers #3 and #4;

FIG. 5 shows experimental results optical intensities of plasma generated at different frequencies (kHz) and different off-duty times;

FIG. 6 shows results of concentration of gas generated under the plasma intensity conditions of FIG. 5;

FIG. 7 shows plasma electrode pad samples for experiment respectively including spacers made of 9 different materials for performance evaluation;

FIG. 8 shows a configuration of a plasma electrode module sample for experiment;

FIG. 9 shows the number of generated plasma dots and the mean area of generated plasma photographed in a dark room after operating a plasma electrode pad according to an experimental example;

FIG. 10 is a table arranging numbers of plasma and mean areas of plasma obtained for the 9 different materials of FIG. 7 in accordance with a test method of FIG. 9;

FIG. 11 shows a figure of 6 different non-woven fabric materials photographed through tomography using a scanning electron microscope;

FIG. 12 shows plasma generation efficiencies obtained after flexible plasma electrodes including spacers made of the non-woven fabric materials shown in FIG. 11 operate, respectively;

FIG. 13 shows test results of a relation between the opening ratio and the plasma generation efficiency in each of the non-woven fabric materials according to FIG. 11;

FIG. 15 shows an ozone emission amount according to a measurement distance as ozone concentration.

DESCRIPTION OF REFERENCE NUMERALS

Figure 14:
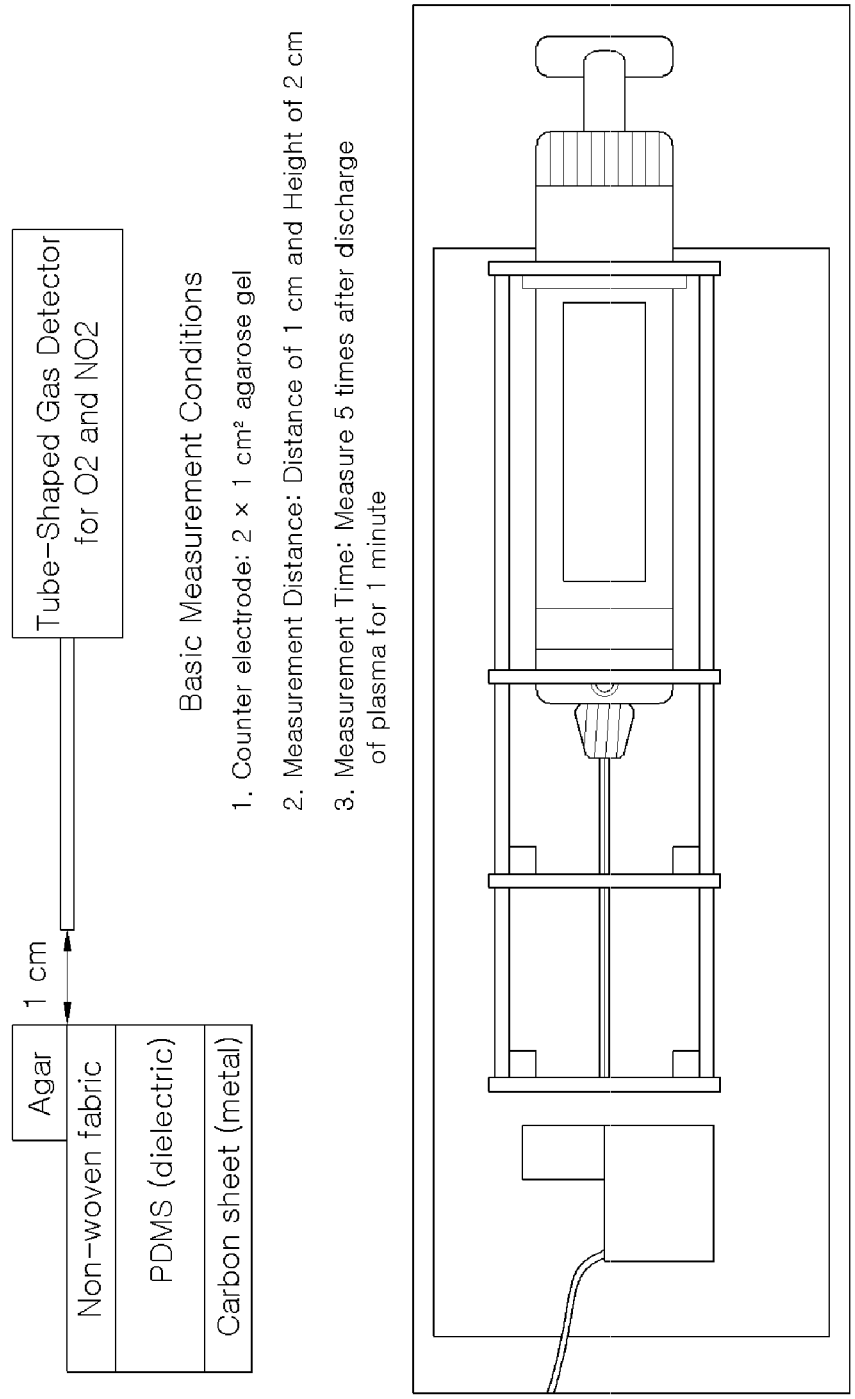
FIG. 14 is a block diagram of a test for measuring gas produced during generation of plasma.

1: Floating Plasma Treatment Device
3: Skin
33: Power Cable
35: Ground Pad
10: Floating Plasma Electrode Pad
100: Adhesive Cover
1001: Adhesive Portion
1003: Through Hole
101: Plasma Electrode
1011: Terminal
103: Dielectric Thin Film
1031, 1051: Functional Coating
105: Spacer

BEST MODE

Reference will now be made in detail to the preferred embodiments of the present invention, examples of which are illustrated in the accompanying drawings. Wherever possible, the same reference numbers will be used throughout the drawings to refer to the same or like parts.

Objects and effects of the present invention may be easily understood or may be more apparent, referring to the following description. However, the objects and effects of the present invention are not limited to the following description. Furthermore, in the following description of the present invention, a detailed description of known functions and configurations incorporated herein will be omitted when it may obscure the subject matter of the present invention.

FIG. 1A illustrates a plasma treatment device 1 according to an embodiment of the present invention, to show a plasma treatment state of the plasma treatment device 1. FIG. 1B illustrates the plasma treatment device 1 according to the embodiment of the present invention, to show a state of a plasma electrode pad 10 used after plasma treatment.

Referring to FIG. 1A, the plasma treatment device 1 may include the plasma electrode pad 10, a ground pad 35, and a power supply 30. In the plasma treatment device 1 according to this embodiment, the skin of the human body functions as a ground electrode and, as such, only one molded electrode is provided at the plasma electrode pad 10. The plasma treatment device 1 according to this embodiment is of a floating type in which plasma is generated between one electrode and the skin 3 of the human body. Accordingly, the electrode module according to this embodiment is distinguished from a direct type (direct barrier discharge (DBD) type) in which plasma is discharged between electrodes, and the discharged plasma is indirectly irradiated onto the skin.

In the plasma treatment device 1 according to this embodiment, the plasma electrode 10 may be separably coupled to the power supply 30. Accordingly, the electrode pad 10 may be configured as a disposable product. In addition, according to this embodiment, the plasma electrode pad 10 may have a compact structure because the plasma electrode pad 10 is of a floating electrode DBD (FE-DBD) type and, as such, no ground electrode is provided at the plasma electrode pad 10. The plasma electrode pad 10 according to this embodiment utilizes the skin of the human body as a ground. The plasma treatment device 1 may be provided with the ground pad 35 to contact the skin of the human body, as a separate nozzle. The ground pad 35 may be connected to the power supply 30 and, as such, may be semi-permanently used together with the plasma treatment device 1.

Briefly, the plasma treatment device 1 according to the illustrated embodiment is of a floating type in which the skin of the human body functions as a ground electrode and, as such, plasma is generated between the skin of the human body and a plasma electrode disposed near the skin of the human body in accordance with a voltage applied to the plasma electrode.

The plasma treatment device 1 includes a plasma electrode 101 (FIG. 2) constituted by a conductive metal thin film, and a flexible dielectric thin film 103 (FIG. 2) made of a polymer material. The dielectric thin film 103 is spaced apart from the skin of the human body by a certain distance such that microdischarge is generated in the space between the dielectric thin film 103 and the skin. In addition, the plasma treatment device 1 includes a spacer 105 (FIG. 2) layered on the dielectric thin film 103, to space the dielectric thin film 103 apart from the skin of the human body by a predetermined distance. The plasma electrode 101, the dielectric thin film 103, and the spacer 105 constitute the plasma electrode pad 10.

In addition, the plasma treatment device 1 includes the power supply 30 for applying a DC voltage to the plasma electrode 101 at a predetermined duty ratio. The plasma treatment device 1 also includes the ground pad 35 connected to the power supply 30 and adapted to contact the skin of the human body. The plasma treatment device 1 outputs plasma having a suitable amount of electromagnetic radiation for human bodies under DC power conditions. The plasma electrode pad 10 according to this embodiment will be described later with reference to FIGS. 2 and 3.

Referring to FIG. 1B, it can be seen that the plasma electrode pad 10 is still used even in a state of being separated from the plasma treatment device 1 after completion of plasma treatment using the plasma treatment device 1, as illustrated in FIG. 1A. Even when the plasma electrode pad 10 according to this embodiment is separated from a power cable 33, the spacer 105 thereof contacting the skin may still protect a wound area. In particular, the spacer 105 is made of a fiber material capable of securing regeneration of tissue for wound healing and, as such, does not provide sense of heterogeneity to the patient.

Even when discharge or pus is generated in a wound area, the spacer 105 may appropriately absorb the generated discharge or pus because the spacer 105 is made of a fiber material. The spacer 105 is firmly attached to the patient by an adhesive cover 100 and, as such, the patient may enjoy daily life. In this regard, the plasma electrode pad 10 according to this embodiment may not only function as an electrode module for plasma treatment for the patient, but also may function as a patch or a band for protecting a wound area for a certain period.

The power supply 30 applies a DC voltage to the plasma electrode pad 10 at a predetermined duty ratio. It is noted that, in the illustrated embodiment, the power supply 30 applies a DC voltage for generation of plasma. Such a DC voltage provides superior electromagnetic stability in association with plasma treatment, as compared to use of an AC voltage. In association with evaluation items of safety of medical devices, there is a standard related with electromagnetic waves according to a Notice from the Ministry of Food and Drug Safety associated with "Common Standards for Electromagnetic Safety of Medical Devices". Therefore, the plasma electrode pad 10 should satisfy requirements of the above-described standard, for realization thereof as a medical device for wound treatment. When the power supply 30 is embodied to use AC power, it is very difficult to satisfy requirements of Common Standards for Electromagnetic Safety. However, the DC voltage-based plasma generation module may satisfy electromagnetic safety requirements for stability of human bodies.

In this case, if the DC voltage from the power supply 30 is used as electric power without separate signal processing, a considerable degradation in plasma generation efficiency may occur, as compared to AC power. To this end, in order to achieve an enhancement in plasma generation efficiency in the case of using DC power, the power supply 30 applies a DC voltage taking the form of pulses having a predetermined duty ratio. In this case, although the power supply 30 uses DC power, the power supply 30 may achieve an enhancement in plasma generation efficiency through reproduction of effects of AC power.

In this embodiment, the power supply 30 outputs a DC voltage of more than 0 kV, but not more than 5 kV having a predetermined duty ratio, for generation of plasma. In detail, the power supply 30 according to this embodiment has a pulse frequency of 130 to 150 kHz and an off duty time of 2 to 4 µs. The voltage conditions of the power supply 30 are determined taking into consideration requirements related with ozone emission amount allowed for human bodies in the evaluation items of safety of medical devices. It is noticed that ozone emission in medical devices should be 0.05 ppm or less as a reference for determining whether or not ozone emitted during generation has an appropriate level of potential harmfulness to humans.

Plasma inevitably involves emission of ozone in an ionization process. For this reason, technical issues for minimizing emission of ozone are important in association with realization of the plasma electrode pad 10 for medical devices. Emission of ozone may be minimized by coating a photocatalyst or an active catalyst over the electrode module and appropriately controlling power conditions. Such technical issues will be described in more detail in experimental examples which will be described later. Power conditions of the power supply 30 according to this embodiment may be understood as conditions for reducing the ozone emission amount of the plasma electrode pad 10 according to this embodiment to 0.05 ppm or less.

The plasma treatment device 1 may further include a display 31 for displaying whether or not plasma is generated or intensity of plasma. When the plasma electrode pad 10 comes into contact with the skin, the plasma electrode pad 10 generates plasma, using the skin as a ground electrode, and, as such, the user has difficulty identifying generation of plasma with the naked eye. Accordingly, in order to identify whether or not the plasma electrode pad 10 operates normally, generation of plasma or intensity of plasma may be displayed through the display 31, which is separately provided.

Hereinafter, the plasma electrode pad 10 according to this embodiment will be described.

FIG. 2 is an exploded perspective view of the plasma electrode pad 10 according to the illustrated embodiment of the present invention. FIG. 3 illustrates operation of a floating type plasma pad according to the illustrated embodiment of the present invention.

Referring to FIGS. 2 and 3, the plasma electrode pad 10 is directly attached to the skin 3 to be treated, like a patch. The plasma electrode pad 10 may include the adhesive cover 100, the plasma electrode 101, the dielectric thin film 103, and the spacer 105.

In an embodiment, the plasma electrode pad 10 includes a plasma electrode 101 constituted by a conductive metal thin film, a flexible dielectric thin film 103 made of a polymer material, and spaced apart from the skin of the human body by a predetermined distance, to generate microdischarge in a space defined between the dielectric thin film 103 and the skin of the human body, and a spacer 105 layered on the dielectric thin film 103, to space the dielectric thin film 103 from the skin of the human body by a predetermined distance. The spacer 105 is made of a woven fiber material to form multiple layers of fiber bundles.

In another embodiment, the plasma electrode pad 10 includes a plasma electrode 101 constituted by a conductive metal thin film, a flexible dielectric thin film 103 made of a polymer material, and spaced apart from the skin of the human body by a predetermined distance, to generate microdischarge in a space defined between the dielectric thin film 103 and the skin of the human body, and a spacer 105 layered, at one surface thereof, on the dielectric thin film 103, to space the dielectric thin film 103 from the skin of the human body by a predetermined distance. The spacer 105 has a predetermined opening ratio. The spacer 105 contacts the skin at the other surface thereof such that plasma is directly generated on the skin through cavities formed in the spacer 105 in accordance with the predetermined opening ratio and, as such, the skin is irradiated with the plasma having the form of dots.

Hereinafter, a detailed configuration of the plasma electrode pad 10 according to each embodiment will be described.

Referring to FIG. 2, the flexible plasma electrode pad 10 has a layered structure including the spacer 105, the dielectric thin film 103, the plasma electrode 101 and the adhesive cover 100 sequentially layered in this order from the side of the skin 3.

The adhesive cover 100 functions as a cover of the plasma electrode pad 10. The adhesive cover 100 also functions as an insulation member for the plasma electrode 101. The adhesive cover 100 may be made of a flexible material. In the illustrated embodiment, the material of the adhesive cover 100 may be silicon, polydimethyl-siloxane (PDMS), or synthetic rubber. The adhesive cover 100 may include an adhesive portion 1001 for attachment of the electrode pad 10 to the skin 3. The adhesive cover 100 formed with the adhesive portion 1001 has a greater area than those of the plasma electrode 101, the dielectric thin film 103 and the spacer 105. The adhesive portion 1001 is coated with a well-known adhesive material at a lower surface thereof. The adhesive portion 1001 is attached to the skin 3, to fix the plasma electrode pad 10.

The adhesive cover 100 is formed with a though hole 1003 at a portion thereof. The through hole 1003 allows a power terminal 1011 of the plasma electrode 101 disposed beneath the adhesive cover 100 to be externally exposed.

The plasma electrode 101 is constituted by a conductive metal thin film. Preferably, the plasma electrode 101 is made of a material having superior conductivity and flexibility. For example, copper (Cu) materials are mainly used for plasma electrode modules. However, since the plasma electrode pad 10 according to the illustrated embodiment is positioned near the skin, for medical purposes, it is preferred that the plasma electrode 101 be made of a carbon material, as compared to a copper (Cu) material exhibiting severe generation of heat and low durability.

The plasma electrode 101 may include a terminal 1011 for connection of the plasma electrode 101 to the power cable 33. The terminal 1011 may be configured to take the form of a button such that the terminal 1001 protrudes upwards. The terminal 1011 may be provided at a distal portion of the plasma electrode 101 in a planar direction of the plasma electrode 101. In this case, however, there is convenience in that the power cable 33 should be connected to a thin side portion of the plasma electrode pad 10. Furthermore, in the case in which the terminal is exposed from the distal portion of the plasma electrode pad 10 after separation of the power cable 33 from the plasma electrode pad 10, the exposed terminal may be unpleasant to the patient. To this end, in the illustrated embodiment, the terminal 1011 is configured to protrude upwards from the plasma electrode 101.

The dielectric thin film 103 is made of a polymer material to have flexibility, and is layered on the plasma electrode 101. The dielectric thin film 103 is spaced apart from the skin of the human body by a predetermined distance, to generate microdischarge in a space defined between the dielectric thin film 103 and the skin of the human body.

Generally, a rigid material is used as a dielectric in plasma electrodes. On the other hand, there are few cases that products in which a polymer material is used as a dielectric material of a plasma electrode are commercially available. This is because a rigid dielectric generally used has a high dielectric constant of 6 to 10 and, as such, provides an advantage of easy generation of plasma. However, a rigid dielectric has a problem in that a great amount of ozone ($O_3$) is emitted during generation of plasma due to the high dielectric constant of the rigid dielectric. This causes difficulty in medical engineering application intended in the present invention. On the other hand, polymer materials have low dielectric constants and, as such, exhibit flexible properties even though generation of plasma is difficult.

In the illustrated embodiment, the dielectric thin film 103 may be made of polydimethyl-siloxane (PDMS) or polyimide (PI). The dielectric thin film 103 exhibits better flexibility at a smaller thickness thereof. However, when the dielectric thin film 103 is excessively thin, the high voltage range for generation of plasma may become a breakdown voltage and, as such, a dielectric breakdown phenomenon may occur. In order to avoid such a phenomenon, the voltage breakdown thickness of each material should be taken into consideration. Polymer materials exhibit different voltage breakdown thicknesses in accordance with properties thereof. PDMS and PI, which are used as polymer materials in the illustrated embodiment, do not generate voltage breakdown only when they have a minimum thickness of 0.1 mm or more. Therefore, it is preferred that the dielectric thin film 103 be formed to have a thickness not less than 0.1 mm, but less than 1 mm for securing of flexibility.

The dielectric thin film 103 may be coated with photocatalyst particles or active catalyst particles for absorption of ozone. The dielectric thin film 103 may be provided with a functional coating 1031 constituted by a photocatalyst or an active catalyst for a reduction in ozone emission. In this case, $TiO_2$ or $MnO_2$ may be included in the catalyst material.

The spacer 105 is layered on the dielectric thin film 103, to space the dielectric thin film 103 from the skin of the human body by a predetermined distance. In this case, the spacer 105 has a feature in that the spacer 105 is made of a woven fiber material to form multiple layers of fiber bundles. In the plasma electrode pad 10 according to the illustrated embodiment using the floating type DBD plasma electrode structure in which the skin 3 of the human body is used as a ground electrode, a certain space should be present between the dielectric thin film 103 and the skin 3. Only when such a space is present, may atmospheric plasma be formed in the space. To this end, the plasma electrode pad 10 is provided with the configuration of the spacer 105 for spacing the dielectric thin film 103 from the skin 3. In connection with this, the space is essentially required and, as such, the spacer generally has a mesh structure having through holes. That is, those skilled in the art will naturally appreciate, as the spacer, use of a mesh thin film having through holes able to be macroscopically observed. However, in accordance with results of tests conducted for various materials, as in experimental examples to be described later, the inventors identified that a fiber material having a complicated structure distinguished from conventional theoretical mesh structures more effectively functions as a spacer for generation of plasma, as compared to the conventional theoretical mesh structures. A spacer having a random complicated structure exhibits excellent plasma generation effects, as can be seen from the following experimental examples, differently from an expectation that, in the fiber material having the complicated structure, there are few through holes able to be macroscopically observed and, as such, plasma cannot be generated.

In this regard, the spacer 105 according to the illustrated embodiment has a feature in that the spacer 105 is made of a fiber material to form multiple layers of fiber bundles. In this case, plasma is generated in spaces defined between the fiber bundles. The spacer 105 has a random complicated structure including multiple layers of fiber bundles. In the present disclosure, the opening ratio is defined by the ratio of the space opened between fibers constituting the multiple layers to an open portion of the space occupied by the fibers in a cross-section of the multiple layers viewed from the top side. The spacer 105 according to the illustrated embodiment preferably has an opening ratio of 30% or more. Referring to results of tests conducted for materials having opening ratios under various conditions, it can be seen that opening ratio and plasma generation efficiency have a low proportional relation in an opening ratio range of 20% or less while having an improved proportional relation in an opening ratio range of 20 to 30%, and a high plasma generation efficiency is exhibited in an opening ratio range of 30% or more. In this regards, it may be considered that there is a considerable critical meaning of the plasma generation efficiency under the condition that the opening ratio is 30% or more. The spacer 105 according to this embodiment is made of a fiber material forming a random complicated structure of multiple layers, and has an opening ratio of 30% or more.

In more detail, the spacer 105 is preferably made of a non-woven fabric material. Non-woven fabrics have multiple layers of fiber bundles and, as such, are distinguished from gauzes woven to have a mesh structure, using rayon or synthetic fibers. The reason why a non-woven fabric material is suitable for the spacer 105, as compared to a gauze having a mesh structure is as follows. First, the plasma generation efficiency of the non-woven fiber material is superior to that of the mesh structure, referring to the experimental examples to be described later. Second, in the mesh structure, the area of each through hole is great. In this case, the distance between the mesh structure and the skin 3 corresponds to the thickness of a single layer of woven fibers. On the other hand, in the case of a non-woven fabric having a multilayer structure of a plurality of fiber bundles, the fiber bundles, which are woven in an entangled state, form a plurality of layers such that random spaces are formed among the fiber bundles. When the spacer 105 to be attached to the skin is constituted by the mesh structure, the dielectric thin film 103 closely contacts large-size through holes of the mesh structure in a bonding process and, as such, there may be possibility that the efficiency of the plasma generation space is degraded. On the other hand, in the case of the non-woven fabric, the dielectric thin film 103 has difficulty directly contacting the skin even when the non-woven fabric is forcibly pressed onto the skin for bonding thereof to the skin, because the fiber bundles constitute a multilayer structure. Accordingly, it may be possible to more hygienically protect a wound area of the skin 3 in accordance with application of the non-woven fabric material to the spacer 105. In this case, the plasma generation efficiency is also excellent. Third, the non-woven fabric, which is constituted by a plurality of fiber bundles, may reduce emission of ozone in accordance with characteristics of the material thereof. The spacer 105 according to the illustrated embodiment maintains the concentration of ozone emitted around plasma to be 0.05 or less. This may be achieved by coating photocatalyst particles or active catalyst particles for ozone absorption over the spacer 105. The spacer 105 may include a functional coating 1051 constituted by a photocatalyst or an active catalyst for a reduction in ozone emission amount. In this case, the catalyst may include $TiO_2$ or $MnO_2$. Fourth, in the illustrated embodiment in which the non-woven fabric is used as the spacer 105, a maximum photocatalyst coating efficiency may be obtained. In the illustrated embodiment, photocatalyst particles are coated over the non-woven fabric in a spray manner. In this case, the photocatalyst particles are attached to the multilayer fiber bundles and, as such, maximum ozone absorption performance is obtained. However, in the case of a spacer having a mesh structure, the photocatalyst coating area thereof is small.

FIG. 3 illustrates operation of the plasma electrode pad 10 according to the illustrated embodiment. Referring to FIG. 3, in practice, plasma P formed on the surface of the skin 3 takes the form of dots. For better understanding, the formation figure of the plasma P viewed from the bottom of the spacer 105 is shown in an exploded state in FIG. 3.

Hereinafter, an experimental example as to electric power conditions of the power supply 30 according to the illustrated embodiment, an experimental example as to conditions of the material of the spacer 105, and an experimental example as to checking of ozone and active oxygen will be described.

Experimental Example 1. Electric Power Conditions of Power Supply

In this experiment, the duty ratio and frequency of pulses as optimal efficiency conditions for plasma generation according to characteristics of the power supply 30 using DC power are identified.

FIG. 4A shows identified results obtained after an experiment is conducted for four transformers having different turn ratios while varying frequency (kHz) and duty ratio (μs), to identify conditions in which high output characteristics are maintained. FIG. 4A shows identified results of power characteristics of transformers #1 and #2. FIG. 4B shows identified results obtained after an experiment is conducted for four transformers having different turn ratios while varying frequency (kHz) and duty ratio (μs), to identify conditions in which high output characteristics are maintained. FIG. 4B shows identified results of power characteristics of transformers #3 and #4. Referring to results of FIGS. 4A and 4B, it can be seen that generation of plasma is possible in a frequency range of 100 to 160 kHz in the four transformers having different turn ratios in common.

FIG. 5 shows experimental results of optical intensities of plasma generated at different frequencies (kHz) and different off-duty times. In FIG. 5, "X plasma intensity" and "Y plasma intensity" are conditions selected through variation in optical intensity of plasma according to variations in frequency and off-duty time. These conditions determine whether or not ozone is contained in an amount of 0.05 ppm or less in gas produced during generation of plasma. Based on these conditions, plasma generation conditions are sorted.

Measurement of optical intensity of plasma is based on measured results of optical emission spectroscopy (@360 nm). In measurement of optical intensity of plasma, light having a wavelength of 360 nm was selected from light of various wavelengths generated from atmospheric plasma, and a variation in optical intensity of the selected light under different conditions was observed. Optical intensity ranges in which ozone is emitted in an amount of 0.05 ppm or less under the condition that generation of plasma is possible were indicated as "Y plasma intensity" zones.

FIG. 6 shows results of concentration of gas generated under the plasma intensity conditions of FIG. 5. FIG. 6 depicts amounts of $O_3$ and $NO_2$ generated in an X plasma intensity zone in association with spacers 105 made of different materials and amounts of $O_3$ and $NO_2$ generated in the X plasma intensity zone when each spacer 105 includes photocatalyst functional layers 1031 and 1051. In this case, materials OLC15, OCP16, OCP22, OCP30, OCP40 and CCT50 respectively selected from the spacers 105 are non-woven fabric materials. An experimental example conducted for the selected materials will be described later. Meanwhile, it is preferred that $O_3$ be generated in an amount of 0.05 ppm or less. On the other hand, it is desirable for $NO_2$ to be generated as much as possible because $NO_2$ is an active gas useful for sterilization.

Referring to FIG. 6, it can be seen that, even when a photocatalyst functional layer for absorption of ozone is coated, the amount of ozone emitted in the X plasma intensity zone exceeds 0.05 ppm. On the other hand, it can be seen that, when the non-woven fabric materials of OCL15, OCP16, OCP40, and CCT50 are used, the amount of ozone emitted in the Y plasma intensity zone is 0.05 ppm or less. In particular, it is noted that the ozone emission amount and the carbon dioxide generation amount in the X plasma intensity range are similar. On the other hand, in the Y plasma intensity zone, the ozone emission amount is reduced, whereas the carbon dioxide generation amount is relatively great.

Operation conditions of the power supply 30 in the X plasma intensity zone are a frequency of 120 kHz, an off-duty time of 5.08 µs, a plasma turn-on time of 0.426 ms, and a voltage of 0 to 7 kV. Operation conditions of the power supply 30 in the Y plasma intensity zone are a frequency of 140 kHz, an off-duty time of 2.64 µs, a plasma turn-on time of 0.426 ms, and a voltage of 0 to 4 kV.

In accordance with experimental results of FIGS. 4A to 6, in the power supply 30 according to the illustrated embodiment, the pulse frequency thereof is 130 to 150 kHz, and the off-duty time thereof is 2 to 4 µs.

Experimental Example 2. Plasma Generation Efficiency Experiment for Different Spacer Materials 2-1. Mesh Structure vs. Complicated Structure FIG. 7 shows plasma electrode pad samples for experiment respectively including spacers made of 9 different materials for performance evaluation. FIG. 8 shows a configuration of a plasma electrode module sample for experiment. Referring to FIG. 8, an agarose gel was used as a configuration functioning as a ground and corresponding to the skin of the human body. In the flexible plasma electrode pad according to this experimental example, plasma is generated only when the plasma electrode pad contacts the human body. In order to externally identify such a phenomenon, a transparent agarose gel was used. The agarose gel was produced by hardening a mixture of agar powder/deionized (DI) water 10 wt. % at 70° C.

As a configuration corresponding to the spacer in FIG. 8, flexible plasma pads respectively using 9 different materials of FIG. 7 were manufactured, and were subjected to a plasma generation test. The 9 different materials shown in FIG. 7 are sequentially designated by serial numbers in a direction from left to right and in a direction from top to bottom. The names of the materials are as follows.

TABLE 1

| Serial Number | Name of Material |
| --- | --- |
| 1 | PE mesh |
| 2 | non-woven fabric, pp-30 w |
| 3 | non-woven fabric, smms-15 w |
| 4 | non-woven fabric |
| 5 | pp mesh |
| 6 | pp mesh, pp50 |
| 7 | pp mesh, pp70 |
| 8 | pp mesh, pp30 |
| 9 | pp mesh, pp70 |

All the materials of Serial Number 1, and Serial Numbers 5 to 9 are mesh structures. The materials of Serial Numbers 2 to 4 are non-woven fabrics each including multiple layers of non-woven fiber bundles. FIG. 9 shows the number of generated plasma dots and the mean area of generated plasma photographed in a dark room after operating a plasma electrode pad according to the experimental example. Photographs of FIG. 9 show a plasma generation figure when the non-woven fabric of Serial Number 3 is used.

FIG. 10 is a table arranging numbers of plasma and mean areas of plasma obtained for the 9 different materials of FIG. 7 in accordance with the test method of FIG. 9. Referring to FIG. 10, the materials of Serial Numbers 3, 6 and 7 were identified as materials exhibiting excellent results in terms of both the plasma number and the plasma area.

It is noted that dot-shaped plasma is discharged in the non-woven material as shown in FIG. 9, differently from theoretical expectation. This is because the non-woven materials of Serial Numbers 2 to 4, which discharge dot-shaped plasma, are different from materials formed with through holes. In the mesh structures as Serial Number 1 and Serial Numbers 5 to 9, it is natural that plasma having a shape corresponding to the shape of through holes of meshes is discharged. In addition, for the plasma area in the test method of FIG. 9, only the plasma area of 10 pixel$^2$ or more was selected. In connection with this, Serial Number 3 exhibited a minimum variation in plasma number and a minimum variation in plasma area, differently from Serial Numbers 6 and 7. From these results, it may be expected that the dot performance capable of generating each plasma dot having an area of 10 pixel$^2$ or more in the checked number of plasma dots is superior. In addition to the plasma generation efficiency as described above, the non-woven materials are more suitable for a plasma electrode pad for wound treatment by virtue of the above-described second and fourth reasons. In this regard, the material having a randomly-entangled complicated structure constituted by multiple layers of fiber bundles may be more excellent, as compared to the material having a mesh structure.

2-2. Plasma Characteristics of Non-Woven Fabric Material Having Complicated Structure Under Different Conditions FIG. 11 shows a figure of 6 different non-woven fabric materials photographed through tomography using a scanning electron microscope. The 6 non-woven fabric materials are as follows.

TABLE 2

| Name of Material | Thickness | Fiber Diameter |
| --- | --- | --- |
| OCL15 | 60 µm | 15 µm |
| OCP16 | 70 µm | 15 µm |
| OCP22 | 80 µm | 15 µm |
| OCP30 | 110 µm | 15 µm |
| OCP40 | 150 µm | 15 µm |
| CCT50 | 180 µm | 15 µm |

FIG. 12 shows plasma generation efficiencies obtained after flexible plasma electrodes including spacers made of the non-woven fabric materials shown in FIG. 11 operate, respectively. Referring to FIG. 12, in the case of the non-woven fabric material as OCL15, plasma was discharged, like glow discharge, without producing streamers (filaments) and, as such, it was impossible to calculate the number of generated plasma dots. It may be estimated that generation of plasma in the form of glow discharge was caused by a reduction in discharge voltage occurring due to the fact that the thickness of the non-woven fabric material of OCL15 is smallest, and as such, the distance between electrodes is excessively small.

FIG. 13 shows test results of a relation between the opening ratio and the plasma generation efficiency in each of the non-woven fabric materials according to FIG. 11. In a diagram of FIG. 13, the right y-axis represents the opening ratio (%), and the left y-axis represents the number of plasma discharged in the form of dots, namely, plasma dots each having an area of 10 pixel² or more. In this case, the opening ratio is a numerical value quantified by the ratio of an opened space to an area formed by fiber bundles in an image photographed through tomography using a scanning electron microscope.

It is noted that, when the opening ratio of the non-woven fabric material is 20% or less, the plasma generation efficiency was linearly exhibited, but was not exhibited to be high. The diagram of FIG. 13 shows that the plasma generation efficiency increases as the opening ratio becomes greater. However, the opening ratio and the plasma generation efficiency did not increase linearly throughout entireties thereof, and the plasma generation efficiency increased, starting from the opening ratio of 30% or more. After combining the results of FIGS. 11 to 13, it can be seen that glow discharge occurs at a thickness of 60 µm or less as in OCL15. Accordingly, it may be summarized that most effective plasma is generated at an opening ratio of 30% or more in a thickness range of 60 to 100 µm.

Experimental Example 3. Gas Generation Amount Test

FIG. 14 is a block diagram of a test for measuring gas produced during generation of plasma. It is assumed that gas to be measured includes harmful ozone and useful carbon dioxide. As electric power conditions for initial gas measurement, a frequency of 120 kHz, a duty time of 5.08 µs, and a delay time of 0.426 ms were set. An agarose gel of 2×1 cm² was used as a ground electrode corresponding to the skin. Measurement was repeatedly conducted 5 times after plasma discharge for 1 minute under the condition that a measurement distance including a spacing of at least 1 cm and a height of 2 cm was maintained.

For the plasma electrode pad used in the test, a PDMS material was used as a dielectric thin film, and a carbon material was used as a plasma electrode. In addition, a photocatalyst was coated over the PDMS and the spacer and, as such, the test was conducted under superior ozone absorption conditions. FIG. 15 shows an ozone emission amount according to a measurement distance as ozone concentration. Referring to FIG. 15, it can be seen that, as the distance between the electrode and a gas detector increases at intervals of 1 cm, the ozone emission amount is further greatly reduced. In accordance with Framework Act on Environmental Policy and Standard related with indoor air cleaners, measurement for evaluation of ozone emission amount is conducted in a chamber for dust collection tests or an indoor space having a spatial volume of 40 m³±10 m³ (a ceiling height of 3 m or less). These test conditions are based on a problem occurring when ozone comes into the respiratory organ of a human. The plasma electrode pad 10 according to the illustrated embodiment is attached to the skin. Even when the plasma electrode pad 10 is applied to the face, the plasma electrode pad 10 may be spaced apart from the nose or the mouth, which are respiratory organs of the human body, by a distance of 1 to 3 cm or more. Referring to test results of FIG. 15, the ozone emission amount is 0.05 ppm or less even when the distance from the plasma electrode pad is only 3 cm.

However, in order to secure maximum stability, conditions that ozone emission is maintained within 0.05 ppm or less even when the distance between the plasma electrode pad and the tube-shaped detector is 1 cm or less were determined as optimum conditions in the present experimental example. Results obtained under the above-described conditions may be identified through an experiment conducted under different conditions of the power supply 30 according to FIG. 6 as described above. FIG. 6 shows results obtained after measurement is conducted under the condition that the tube-shaped detector is spaced by 1 cm, as in the test block diagram of FIG. 14. As the thickness of each non-woven fabric was gradually increased, the concentration trend line of generated gas exhibited characteristics of gradual reduction. Referring to results of this experiment, ozone emission of 0.05 ppm or less was detected even at a measurement distance of 1 cm when OCL15, OCP16, OCP40 and CCT50 were used as spacers.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A floating type plasma electrode pad using the skin of a human body as a ground electrode such that plasma is generated between the skin of the human body and a plasma electrode disposed near the skin of the human body in accordance with a voltage applied to the plasma electrode, comprising:
    the plasma electrode made of a conductive metal thin film;
    a flexible dielectric thin film layered on the plasma electrode, and made of a polymer material, the dielectric thin film being spaced apart from the skin of the human body by a predetermined distance such that microdischarge is generated in a space defined between the dielectric thin film and the skin of the human body; and
    a spacer layered on the dielectric thin film, to space the dielectric film from the skin of the human body by the predetermined distance,
    wherein the spacer is made of a fiber material to form multiple layers of fiber bundles.

2. The floating type plasma electrode pad according to claim 1, further comprising:
    a power supply for supply electric power to the plasma electrode,
    wherein the power supply outputs a DC voltage of more than 0 kV, but not more than 5 kV having a predetermined duty ratio, for generation of plasma.

3. The floating type plasma electrode pad according to claim 1, wherein the spacer has an opening ratio of 30% or more.

4. The floating type plasma electrode pad according to claim 1, wherein the spacer is coated with photocatalyst particles or active catalyst particles for absorption of ozone.

5. The floating type plasma electrode pad according to claim 1, wherein the dielectric thin film is coated with photocatalyst particles or active catalyst particles for absorption of ozone.

6. The floating type plasma electrode pad according to claim 1, wherein the spacer is made of a non-woven fabric material.

7. The floating type plasma electrode pad according to claim 1, wherein plasma is generated in spaces defined among the fiber bundles of the spacer, and ozone emitted around the plasma has a concentration of 0.05 ppm or less.

8. A floating type plasma treatment device using the skin of a human body as a ground electrode such that plasma is generated between the skin of the human body and a plasma electrode disposed near the skin of the human body in accordance with a voltage applied to the plasma electrode, comprising:

a floating type plasma electrode pad comprising
the plasma electrode made of a conductive metal thin film,
a flexible dielectric thin film layered on the plasma electrode, and made of a polymer material, the dielectric thin film being spaced apart from the skin of the human body by a predetermined distance such that microdischarge is generated in a space defined between the dielectric thin film and the skin of the human body, and
a spacer layered on the dielectric thin film, to space the dielectric film from the skin of the human body by the predetermined distance,
a power supply for supply electric power to the plasma electrode at a predetermined duty ratio; and
a ground pad connected to the power supply, and adapted to contact the skin of the human body,
whereby plasma having an electromagnetic wave emission amount suitable for the human body under a DC power condition.

9. A floating type plasma electrode pad using the skin of a human body as a ground electrode such that plasma is generated between the skin of the human body and a plasma electrode disposed near the skin of the human body in accordance with a voltage applied to the plasma electrode, comprising:

the plasma electrode made of a conductive metal thin film;
a flexible dielectric thin film layered on the plasma electrode, and made of a polymer material, the dielectric thin film being spaced apart from the skin of the human body by a predetermined distance such that microdischarge is generated in a space defined between the dielectric thin film and the skin of the human body; and
a spacer layered on one surface of the dielectric thin film, to space the dielectric film from the skin of the human body by the predetermined distance, the spacer having a predetermined opening ratio,
wherein the spacer contacts the skin at the other surface thereof such that the skin is directly irradiated with the skin through cavities formed at the spacer in a predetermined opening ratio, and the irradiation of the plasma has a dot-shaped form by virtue of the cavities.

* * * * *